United States Patent [19]

Malinouskas

[11] Patent Number: 4,807,630
[45] Date of Patent: Feb. 28, 1989

[54] APPARATUS AND METHOD FOR USE IN PULSE OXIMETERS

[75] Inventor: Donald Malinouskas, Monroe, Conn.

[73] Assignee: Advanced Medical Systems, Inc., Hamden, Conn.

[21] Appl. No.: 107,282

[22] Filed: Oct. 9, 1987

[51] Int. Cl.$^4$ .............................................. A61B 5/00
[52] U.S. Cl. ................................... 128/633; 128/666; 356/41
[58] Field of Search .................. 128/633, 666; 356/41

[56] References Cited

U.S. PATENT DOCUMENTS

| | | | |
|---|---|---|---|
| 3,804,535 | 4/1974 | Rodriguez | 356/217 |
| 3,998,550 | 12/1976 | Konishi | 356/39 |
| 4,167,331 | 9/1979 | Nielsen | 356/39 |
| 4,266,554 | 5/1981 | Hamaquri | 356/41 |
| 4,407,290 | 10/1983 | Wilber | 128/633 |
| 4,586,513 | 5/1986 | Hamaquri | 128/633 |
| 4,653,498 | 3/1987 | New, Jr. et al. | 128/633 |
| 4,694,833 | 9/1987 | Hamaquri | 356/41 |
| 4,714,080 | 12/1987 | Edgar, Jr. et al. | 128/666 |
| 4,714,341 | 12/1987 | Hamaquri et al. | 128/633 |

OTHER PUBLICATIONS

Brooks et al., *Anesthesiology*, 61:630 (1984).
Kim, J. et al., *Anesthesiology*, 63:A174 (1985).
Mackenzie, N., *J. Clin. Monit.*, 1:156–160 (1985).
Nellcor, "Nellcor Technical Note No. 2: Relationship Between Functional and Fractional Saturation," 1984.
Tremper, K. et al., *Anesthesiology*, 63:A175 (1985).
Yelderman et al., *Anesthesiology*, 59:349–353 (1983).

*Primary Examiner*—Lloyd L. King
*Attorney, Agent, or Firm*—Maurice M. Klee

[57] ABSTRACT

A method of exposing a patient's extremity to light of two wavelengths and detecting the absorbance of the extremity at each of the wavelengths is provided comprising the steps of: (a) generating pulses of light having the first wavelength at a first pulse frequency; (b) generating pulses of light having the second wavelength at a second pulse frequency; (c) exposing the extremity to the first and second pulses; (d) producing an electrical signal corresponding to the total amount of light transmitted through the extremity; (e) separating the electrical signal produced in step (d) into a first amplitude-modulated electrical signal at the first pulse frequency and a second amplitude-modulated electrical signal at the second pulse frequency; and (f) demodulating the first and second amplitude-modulated electrical signals to produce a first signal corresponding to the amount of light transmitted through the extremity at the first wavelength and a second signal corresponding to the amount of light transmitted through the extremity at the second wavelength. The method allows the extremity to be exposed to the two wavelengths in the presence of ambient light and essentially eliminates interference problems caused by 60-cycle power sources. Apparatus for practicing the method is also disclosed.

17 Claims, 5 Drawing Sheets

APPARATUS AND METHOD FOR USE IN PULSE OXIMETERS

BACKGROUND OF THE INVENTION

1. Field of the Invention

This invention relates to oximeters and in particular to improved oximeters which are essentially insensitive to ambient light, effectively immune from 60-cycle interference, and electronically less complicated than existing oximeters.

2. Description of the Prior Art

Oximeters are photoelectric devices which measure the oxygen saturation of blood. Historically, these devices were first used in clinical laboratories on samples of blood taken from patients. In recent years, non-invasive oximeters have been developed and are now widely used in intensive care units to monitor critically ill patients and in operating rooms to monitor patients under anesthesia. Early non-invasive devices relied on dialization of the vascular bed in, for example, the patient's ear lobe to obtain a pool of arterial blood upon which to perform the saturation measurement. More recently, non-invasive devices known as "pulse oximeters" have been developed which rely on the patient's pulse to produce a changing amount of arterial blood in, for example, the patient's finger or other selected extremity. See Yelderman et al., "Evaluation of Pulse Oximetry", *Anesthesiology*, 59:349-353 (1983), and Mackenzie, N., "Comparison of a Pulse Oximeter with an Ear Oximeter and an In-Vivo Oximeter", *J. Clin. Monit.*, 1:156-160 (1985).

Pulse oximeters measure oxygen saturation by (1) passing light of two or more selected wavelengths, e.g., a "red" wavelength and an "IR" wavelength, through the patient's extremity, (2) detecting the time-varying light intensity transmitted through the extremity for each of the wavelengths, and (3) calculating oxygen saturation values for the patient's blood using the Lambert-Beers transmittance law and the detected transmitted light intensities at the selected wavelengths.

Prior to the present invention, the patient's extremity has been exposed to the selected wavelengths sequentially, that is, a first light source, such as, a red-emitting LED, has been turned on for a period of time and then turned off, and then a second light source, such as, an IR-emitting LED, has been turned on and then off. See, for example, U.S. Pat. Nos. 4,167,331 and 4,407,290. Alternatively, it has been proposed to pass broadband light through the extremity and separate the transmitted light into two components using appropriate filters. See U.S. Pat. No. 3,998,550.

Each of these approaches leads to complex and/or expensive devices. For example, filters which are able to adequately separate IR from red light are generally expensive. Also, two light sensors, one for each wavelength, are required for the filter approach. Accordingly, with this approach, it is difficult to produce an inexpensive, disposable sensor module, as is required for operating room and other uses.

In the case of the sequential exposure approach, the apparatus must keep track of which light source is active. This involves deploying switches throughout the signal processing portion of the apparatus whose states are changed as the different sources become active. In addition, delay or "dead" times must be incorporated in the system to ensure that the measured transmittance relates to just the source which is currently active and not to a combination of the two sources. Moreover, the sources must be switched rapidly and the delay times must be kept short so that within each on-off/on-off cycle, the amount of blood and other characteristics of the patient's extremity remain essentially constant.

In addition to the foregoing, both approaches suffer from interference problems due to ambient light and 60-cycle power sources. In particular, changing amounts of ambient red and/or IR radiation can lead to errors in the oxygen saturation measurement. Both of these radiations are normally present in, for example, an operating room as a result of general lighting and IR heating devices. Variations in the levels of these radiations at the location of the oximetry sensor can result from such simple activities as movement of personnel or equipment within the operating room. Moreover, even constant amounts of these background radiations pose problems for existing oximeters since they can saturate the sensor and/or lead to low signal to noise ratios.

In an attempt to deal with the ambient radiation problem, existing oximeters have incorporated complicated circuitry to compensate for background radiation and have placed the sensors in hoods or other packages designed to minimize the amount of ambient light which can reach the sensor element. Notwithstanding these extensive efforts, as has been reported in the medical literature, the oximeters in use today can give false readings or can completely fail to function due to ambient radiation. See Brooks et al., "Infrared Heat Lamps Interfere with Pulse Oximeters," *Anesthesiology*, 61:630 (1984).

In addition to the ambient radiation problem, existing oximeters are also highly sensitive to 60-cycle interference. This high sensitivity is due to the fact that oximeters measure the changes in transmittance resulting from pulsatile blood flow in the patient's extremities, and the frequency content of such pulsatile blood flow ranges up to about 50-60 cycles per second. Accordingly, with the existing approaches, it is difficult to filter out 60-cycle interference using high pass filters since such filters would also filter out part of the signal being measured. To try to deal with this problem, oximeter manufacturers have shielded the sensors and the cables for the sensors. Such shields obviously increase the overall cost of the oximeter. Also, as is commonly known, complete removal of 60-cycle interference is extremely difficult to achieve with shielding, especially in the case of sensors which are attached to patients.

SUMMARY OF THE INVENTION

In view of the foregoing state of the art, it is an object of this invention to provide improved oximeters which are essentially immune from interference problems due to ambient light and 60-cycle power sources. More particularly, it is an object of the invention to provide improved oximeters in which the sensor can be used in ambient light without special packaging or shielding. It is a further object of the invention to provide improved oximeters which are less complicated than existing oximeters and less expensive to build.

To achieve the foregoing and other objects, the invention, in accordance with certain of its aspects, provides an improved method for exposing a patient's extremity to electromagnetic radiation of two wavelengths, e.g., a red wavelength and an IR wavelength, and detecting the absorbance of the extremity at each of the wavelengths, said method comprising the steps of:

(a) generating first and second pulses of electromagnetic radiation having first and second wavelengths, respectively, the first pulses being generated at a first pulse frequency and the second pulses being generated at a second pulse frequency;

(b) exposing the extremity to the first and second pulses;

(c) producing an electrical signal corresponding to the electromagnetic radiation intensity, including the electromagnetic radiation intensity at the first and second wavelengths, at a selected recording location in the vicinity of the extremity, e.g., in the case of a finger, at a location opposite the side of the finger which is exposed to the pulses;

(d) separating the electrical signal produced in step (c) into a first amplitude-modulated electrical signal at the first pulse frequency and a second amplitude-modulated electrical signal at the second pulse frequency: and (e) demodulating the first and second electrical signals.

In accordance with other of its aspects, the invention provides apparatus for practicing the foregoing method which comprises:

(a) a first light pulse generator for generating pulses of light at the first pulse frequency having the first wavelength:

(b) a second light pulse generator for generating pulses of light at the second pulse frequency having the second wavelength;

(c) means for exposing the patient's extremity to the first and second pulses, e.g., means for attaching a red and an IR LED to the patient's finger;

(d) a transducer responsive to electromagnetic radiation having the first and second wavelengths for producing an electrical signal which is representative of the electromagnetic radiation intensity at the recording location:

(e) a first bandpass filter centered at or near the first pulse frequency for producing the first amplitude-modulated electrical signal;

(f) a second bandpass filter centered at or near the second pulse frequency for producing the second amplitude-modulated electrical signal:

(g) a first demodulator for removing the first pulse frequency from the first amplitude-modulated electrical signal; and (h) a second demodulator for removing the second pulse frequency from the second amplitude-modulated electrical signal.

In certain preferred embodiments, the first and second pulse frequencies are non-mixing frequencies, i.e., they are frequencies whose harmonics do not overlap. In other preferred embodiments, the intensities of the light pulses produced by the first and second light pulse generators are commonly controlled so that simultaneous adjustment of those intensities can be readily performed.

The accompanying drawings, which are incorporated in and constitute part of the specification, illustrate the preferred embodiments of the invention, and together with the description, serve to explain the principles of the invention.

DESCRIPTION OF THE PREFERRED EMBODIMENTS

Figure 1A:
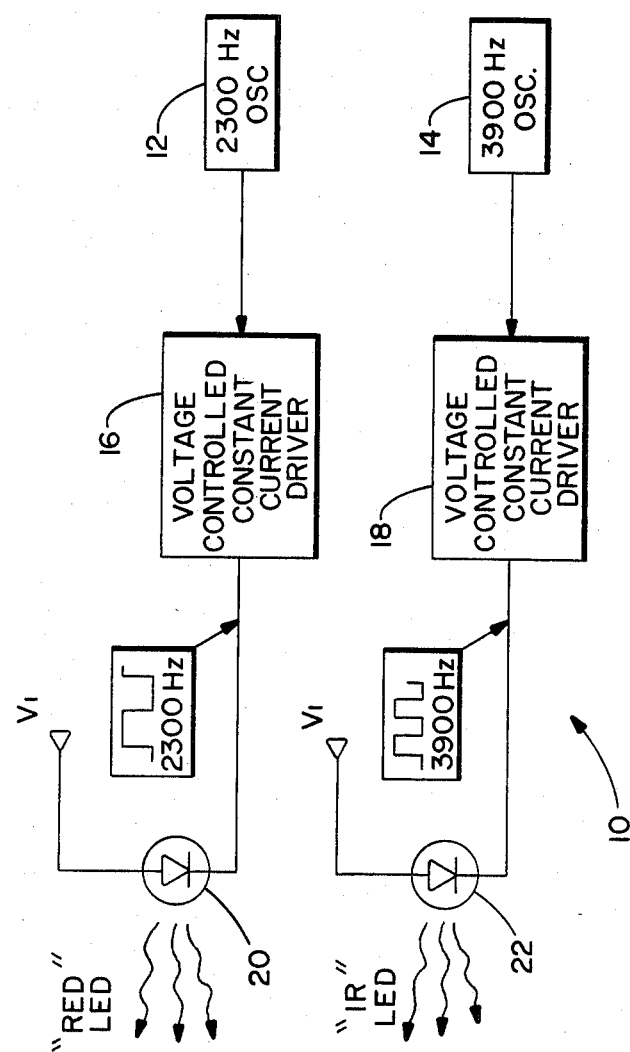
FIGS. 1A and 1B are block diagrams illustrating typical component assemblies which can be used in the pulse generating (FIG. 1A) and pulse detecting (FIG. 1B) portions of the apparatus of the present invention.

With reference to the figures, there is shown in FIG. 1A a block diagram of typical component assemblies which can be used in the practice of the present invention. In particular, FIG. 1A shows a pulse generating assembly 10 for generating pulses of electromagnetic radiation at two different wavelengths, e.g., a red wavelength and an IR wavelength, and at two different pulse frequencies, e.g., 2300 hertz and 3900 hertz.

Assembly 10 includes red and infrared LEDs 20 and 22, voltage controlled constant current drivers 16 and 18 for driving the LEDs, and oscillators 12 and 14 for controlling the constant current drivers. As illustrated in the inserts of FIG. 1A, the oscillators cause the constant current drivers to apply square wave currents to LEDs 20 and 22. The fundamental frequencies of the square wave currents are equal to the frequencies of the oscillators. As a result of the square wave currents, LEDs 20 and 22 produce recurring pulses of infrared and red light at pulse rates which are equal to the oscillator frequencies.

The frequencies of oscillators 12 and 14 are chosen to be non-mixing, that is, the frequencies are chosen so as not to have overlapping harmonics and, in particular, not to have overlapping odd harmonics. The avoidance of overlapping odd harmonics is important because square waves carry energy at the fundamental frequency and the odd harmonics of that frequency. Accordingly, if the frequencies of oscillators 12 and 14 did mix, it would be difficult to adequately separate the electrical signals produced by LED 20's light pulses from those produced by LED 22's light pulses.

The frequencies of oscillators 12 and 14 are also chosen to be substantially above 60 cycles per second so that the filtering in detector assembly 24 (see FIG. 1B) of the electrical signal produced by transducer 13 (see discussion below) removes 60-cycle interference. On the other hand, the frequencies of the oscillators are not made excessively high to avoid the need for complex oscillator circuits. In practice, frequencies on the order of 2300 cycles per second and 3900 cycles per second have been found to work successfully. The first three odd harmonics of these frequencies are 6900, 11,500, and 16,100 hertz and 11,700, 19,500, and 27,300 hertz, respectively, and thus the frequencies are non-mixing. Other frequencies besides 2300 and 3900 hertz of course can be used in the practice of the present invention.

Voltage controlled constant current drivers are used in assembly 10 so that the intensities of the light pulses produced by the LEDs can be controlled. Preferably, the same control voltage is applied to each of drivers 16 and 18 so that the intensities of the pulses produced by LEDs 20 and 22 can be varied simultaneously. This simultaneous control means that the signal processing portion of the oximeter does not have to keep track of the individual intensities of the light produced by the red and infrared LEDs. To applicant's knowledge, such simultaneous control was not employed in prior art oximeters and, in particular, was not employed in prior art oximeters which sequentially activated the red and IR LEDs.

Figure 2:
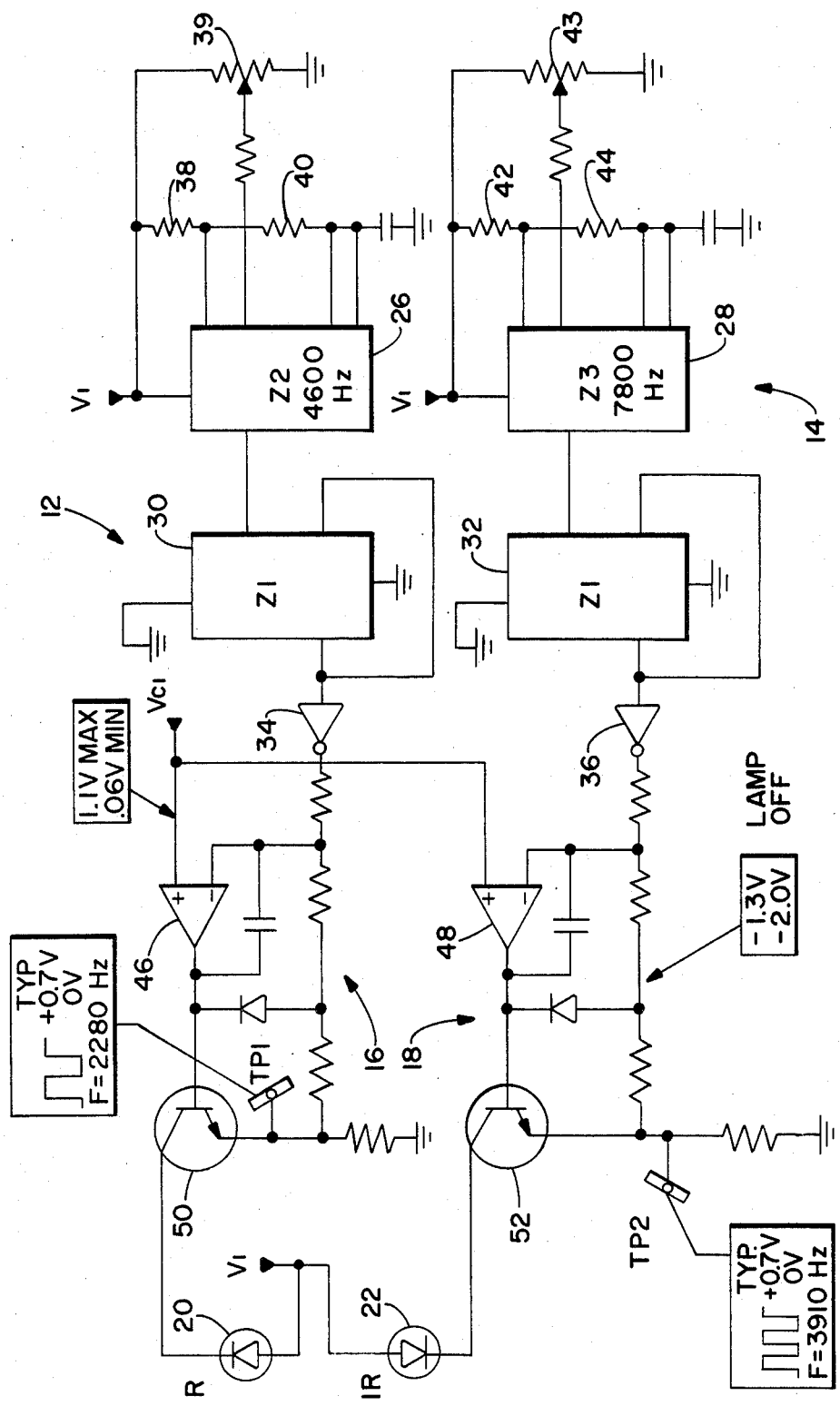
FIG. 2 shows specific components which can be employed in the pulse generating portion of FIG. 1A.

FIG. 2 shows specific components which can be employed in assembly 10. As shown in this figure, oscillators 12,14 can comprise timers 26,28 which oscillate at approximately 4600 hertz and 7800 hertz, respectively, J-K flip-flops 30,32 which divide the output frequencies of the timers in half, and buffers 34,36 which provide a stable signal and sufficient input current for the constant current drivers. A clean power supply (not shown) is used to generate driving voltage $V_1$ for timers 26,28. This same voltage, which can be on the order of +5 volts, is also applied to LEDs 20 and 22. An additional clean power supply (not shown) is used to provide operating current to the operational amplifiers shown in FIG. 2, as well as those shown in FIGS. 3 and 4.

The oscillation frequencies of timers 26,28 are determined through the selection of resistors 38,39,40 and 42,43,44, respectively. Otherwise, matched circuit components are used to generate the IR and infrared light pulses. (Matched circuit components are also used in the rectifier and low pass filter circuits of FIG. 4.) The timer 26,28 and flip-flop 30,32 combination is used to provide a square wave signal having on and off periods which are as equal as possible. This minimizes the amount of even harmonics in the signal generated by transducer 13 and thus enhances the ability to separate the signal corresponding to red light impinging on the transducer from the signal corresponding to the impingement of infrared light.

As shown in FIG. 2, the output of buffers 34,36 is fed into voltage controlled constant current drivers 16,18 which, as illustrated, comprise high speed operational amplifiers 46,48, which compare control voltage $V_{C1}$ with the output of buffers 34,36, and transistors 50,52, whose bases are connected to the output of the operational amplifiers. The resulting current flows through LEDs 20 and 22 are illustrated by the waveform inserts shown at taps TP1 and TP2. As shown in these inserts, pulses of current at a pulse frequency of approximately 2300 hertz pass through LED 20, while pulses of current of essentially the same magnitude but having a frequency of approximately 3900 hertz pass through LED 22.

The pulses of current through LEDs 20 and 22 produce pulses of light which are simultaneously passed through and/or reflected from an extremity of the patient, e.g., the patient's index finger, and then detected by transducer 13 and detector assembly 24. In practice, transducer 13 and LEDs 20 and 22 are adhesively mounted on the patient's extremity and connected to the remainder of the oximetry apparatus by cables. Alternatively, a hood or other mounting means can be used to position the LEDs and the transducer on the extremity.

Although a shielded cable does not have to be used with the transducer since detector assembly 24 removes 60-cycle interference, such a cable can be employed, if desired, to even further reduce the possibility of interference. Similarly, although the transducer does not have to be shielded from ambient light since the detector assembly is tuned to respond only to pulses of light having the frequencies of oscillators 12 and 14 (see discussion below), such shielding can be employed, if desired, to further reduce the possibility of ambient light interference.

Transducer 13 is designed to respond to light having the wavelengths produced by each of LED 20 and LED 22. Most conveniently, transducer 13 is a broadband photodetector which is sensitive to, for example, red and infrared light.

Transducer 13 produces an electrical signal which is representative of the intensity of light impinging on the transducer. In the case of light originating from LED 20, the electrical signal will consist of essentially square wave pulses at the frequency of oscillator 12, the intensity of each pulse, and thus the amplitude of the resulting electrical signal produced by transducer 13, being dependent upon the absorption which the pulse underwent in passing from LED 20 to transducer 13. Similarly, in the case of light originating from LED 22, the electrical signal will also consist of essentially square wave pulses, but at a different frequency, i.e., the frequency of oscillator 14. In addition, the amplitude of the square wave electrical pulses corresponding to light emitted by LED 22 will, in general, be different from the amplitude of the square wave electrical pulses corresponding to light emitted by LED 20 because the wavelengths of the light emitted by the two LEDs are different and thus the absorption of the light by the patient's extremity will be different.

As the absorption of the patient's extremity changes in time, e.g., in response to the patient's pulse, the intensities of the light pulses reaching transducer 13 will change. Accordingly, the electrical signals produced by transducer 13 will consist of square wave pulses whose amplitudes change in time. Looked at another way, transducer 13 detects amplitude-modulated light pulses and produces an amplitude-modulated electrical signal consisting of a carrier having a carrier frequency equal to the oscillator frequency used to produce the light pulses and a superimposed modulation signal corresponding to changes in the intensity of the light pulses reaching the transducer, the changes in intensity being caused by changes in the transmission and/or reflection characteristics of the patient's extremity resulting from the patient's pulse.

Because LED 20 and LED 22 are simultaneously producing pulses, the electrical signal produced by transducer 13 will consist of a superposition of amplitude-modulated square wave pulses at the frequency of oscillator 12 and amplitude-modulated square wave pulses at the frequency of oscillator 14. In addition, the electrical signal will include noise generated by ambient light, 60-cycle power lines, and other noise sources. Detector assembly 24 serves the functions of (1) removing the noise and (2) separating the electrical signal corresponding to light emitted from LED 20 from the electrical signal corresponding to light emitted from LED 22.

Figure 1B:
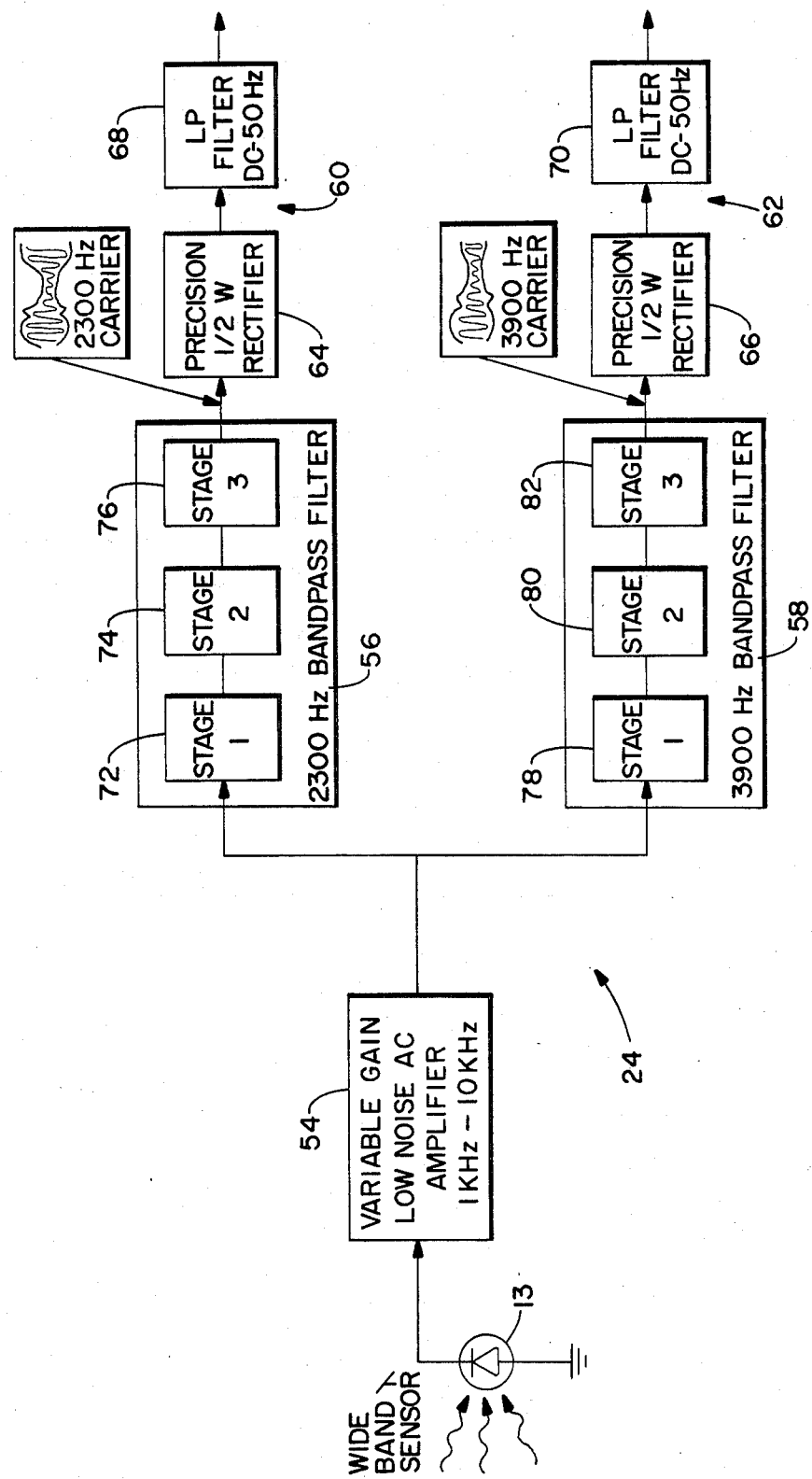

As shown in FIG. 1B, detector assembly 24 includes amplifier 54 for amplifying the signal produced by transducer 13, bandpass filters 56,58, which are tuned to the carrier frequencies produced by oscillators 12 and 14, e.g., 2300 and 3900 hertz, and demodulators 60 and 62 for removing the carrier frequencies from the signals produced by the bandpass filters.

Amplifier 54 preferably has a variable gain to accommodate different baseline levels of light transmission. Also, the amplifier preferably has a low end cut-off frequency substantially above 60 hertz so as to remove 60-cycle and other low frequency interferences, e.g., ambient light interferences, which may be present on the signal produced by transducer 13. (Note that bandpass filters 56,58 also remove low frequency interferences from the final signal produced by detector assembly 24.) The low end cut-off frequency, of course, must be substantially below the lower of the two carrier frequencies. Similarly, the high end cut-off frequency of the amplifier must be substantially above the higher of the two carrier frequencies. In practice, for carrier frequencies of 2300 and 3900 hertz, an amplifier which passes frequencies between about 1 kilohertz and 10 kilohertz has been found to work successfully.

As shown in FIG. 1B, bandpass filters 56,58 each consist of three stages 72,74,76 and 78,80,82, respectively. In practice, the use of three stages has been found adequate to obtain the desired separation between the high carrier and low carrier signals, while still providing sufficient bandwidth about the carrier frequency so as to pass the modulation signal corresponding to changes in light intensity at transducer 13. More or less stages, of course, can be used as desired.

Demodulators 60,62 serve to separate the modulation signal from the carrier signal. A variety of demodulation techniques can be used including rectification followed by low pass filtering, synchronous detection, and the like. The use of rectifiers 64,66 in series with low pass filters 68,70 is illustrated in FIG. 1B. This demodulation technique can be readily implemented in practice and has been found to successfully produce a final signal which accurately represents the changes in absorption of a patient's extremity caused by the patient's pulse.

Figure 3:
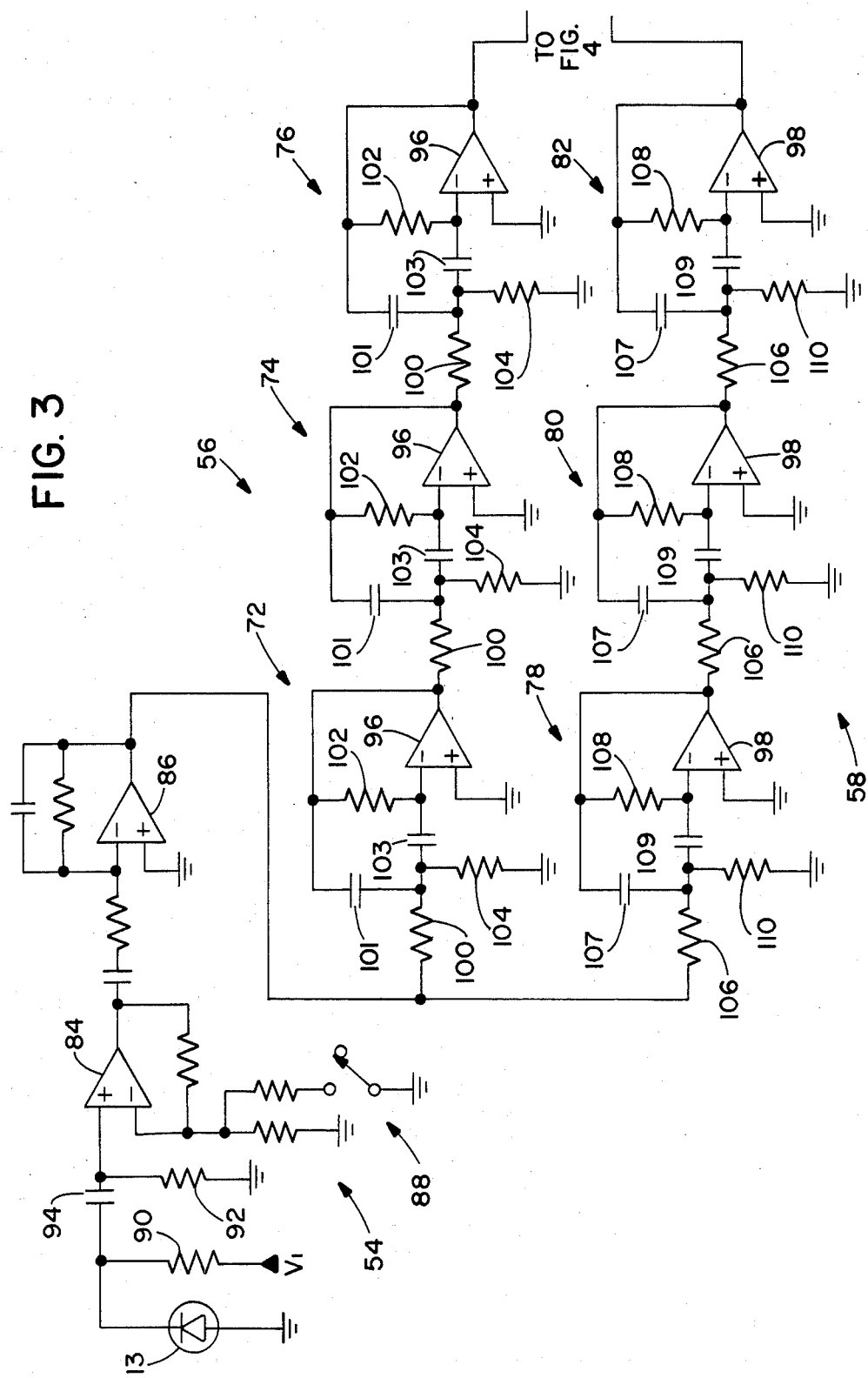
FIGS. 3 and 4 show specific components which can employed in the pulse detecting portion of FIG. 1B.
Figure 4:
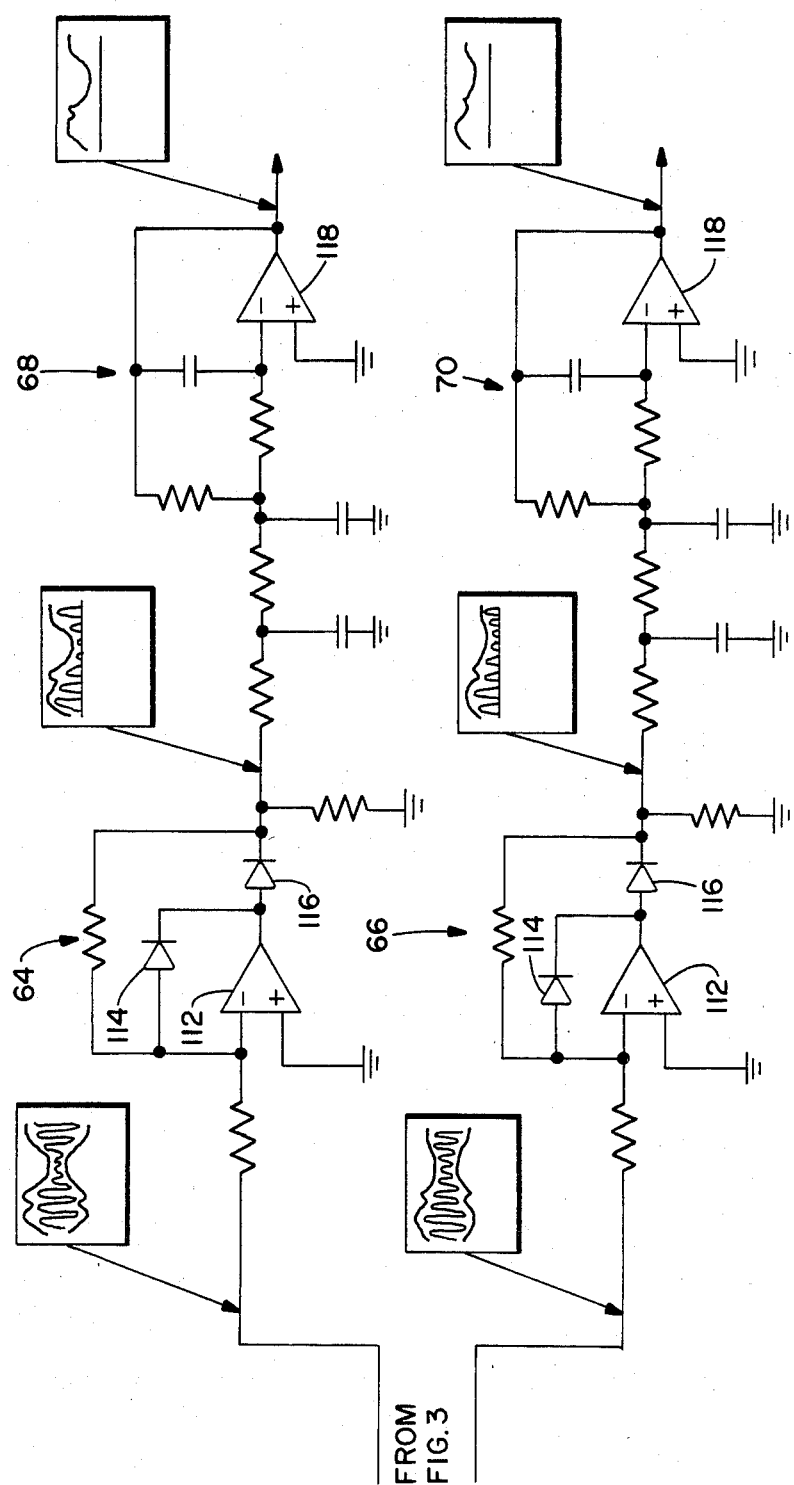

FIGS. 3 and 4 show specific components which can be employed in detector assembly 24. As shown in FIG. 3, amplifier 54 can be a two stage amplifier comprising high speed operational amplifiers 84 and 86. The overall gain of amplifier 54 can be controlled by switch 88, the switch being shown in its low gain position in FIG. 3. Rather than using a manually operated switch, the signal processing portion of the oximeter can control the gain electronically. Resistors 90,92 and capacitor 94 at the head end of amplifier 54 are chosen to provide an input impedance to the amplifier which matches the characteristics of transducer 13.

Bandpass filters 56,58 similarly employ high speed operational amplifiers. The values of resistors 100, 102, and 104 and capacitors 101 and 103 are selected so that the filter stages 72, 74, and 76 are centered at approximately 2300 hertz; similarly, resistors 106, 108, and 110 and capacitors 107 and 109 are selected so that filter stages 78, 80 and 82 are centered at approximately 3900 hertz. In practice, amplifier stages having a gain of approximately 2.0 and a Q value of approximately 7.0 have been found to produce an overall separation greater than $-35$ dB between the 2300 and 3900 hertz signals.

The outputs of the bandpass filters are fed into the rectifier and low pass filter circuits shown in FIG. 4. In particular, high speed operational amplifiers 112 and their associated diodes 114 and 116 strip the negative portions of the signals produced by filters 56 and 58. Operational amplifiers 118 and their associated components form a low pass filter to strip the carrier signal from the rectified signal and produce the final output of the detector assembly. The output signal produced by the detector assembly is suitable for processing by, for example, a microprocessor to calculate and then display the patient's time-varying level of oxygen saturation.

Although specific embodiments of the invention have been described and illustrated, it is to be understood that modifications can be made without departing from the invention's spirit and scope. For example, the invention can be used in fields other than pulse oximetry to expose and record the response of a test specimen to light of more than one wavelength. Also, although the invention has been illustrated in connection with the exposure of a patient's extremity to red and infrared light, electromagnetic radiation having other wavelengths can be used. Similarly, although the use of only two light sources has been illustrated, the invention can be practiced with additional light sources, each operating at its own pulse frequency.

What is claimed is:

1. In a method for performing pulse oximetry wherein a selected extremity of a human being or an animal is exposed to electromagnetic radiation of two different wavelengths, the improvement comprising:
   (a) generating first and second pulses of electromagnetic radiation having first and second wavelengths, respectively, said first pulses being generated at a first pulse frequency and said second pulses being generated at a second pulse frequency:
   (b) exposing the selected extremity to the first and second pulses;
   (c) producing an electrical signal corresponding to the electromagnetic radiation intensity at a selected location in the vicinity of the selected extremity, said electrical signal corresponding to the electromagnetic radiation intensity over a band of wavelengths which includes the first and second wavelengths;
   (d) separating the electrical signal produced in step (c) into a first amplitude-modulated electrical signal at the first pulse frequency and a second amplitude-modulated electrical signal at the second pulse frequency: and
   (e) demodulating the first and second electrical signals.

2. The method of claim 1 wherein the first and second pulse frequencies are non-mixing frequencies.

3. The method of claim 2 wherein the first pulse frequency is approximately 2300 cycles per second and the second pulse frequency is approximately 3900 cycles per second.

4. The method of claim 1 wherein the first wavelength is in the red range and the second wavelength is in the infrared range.

5. Apparatus for use in a pulse oximeter for generating and detecting two wavelengths of electromagnetic radiation comprising:
   (a) first means for generating pulses of electromagnetic radiation having a first wavelength, said pulses being generated at a first pulse frequency;
   (b) second means for generating pulses of electromagnetic radiation having a second wavelength, said pulses being generated at a second pulse frequency:
   (c) means for simultaneously exposing a selected extremity of a human being or an animal to the first and second pulses;
   (d) transducer means for producing an electrical signal which is representative of the electromagnetic radiation intensity at a selected location in the vicinity of the selected extremity, said transducer means being responsive to electromagnetic radiation of the first and second wavelengths;
   (e) first bandpass filter means centered at or near the first pulse frequency operatively connected to the transducer means for separating a first electrical signal from the electrical signal produced by the transducer means, said first electrical signal being representative of the intensity of electromagnetic radiation having the first wavelength at the selected location; and (f) second bandpass filter means centered at or near the second pulse frequency operatively connected to the transducer means for separating a second electrical signal from the electrical signal produced by the transducer means, said second electrical signal being representative of the intensity of electromagnetic radiation having the second wavelength at the selected location.

6. The apparatus of claim 5 further including first demodulating means operatively connected to the first bandpass filter means for removing the first pulse frequency from the electrical signal produced by said filter means and second demodulating means operatively connected to the second bandpass filter means for removing the second pulse frequency from the electrical signal produced by said filter means.

7. The apparatus of claim 6 wherein the first demodulating means includes a first half-wave rectifier in series with a first low pass filter and wherein the second demodulating means includes a second half-wave rectifier in series with a second low pass filter.

8. The apparatus of claim 5 wherein the first means includes a first oscillator in series with a first frequency divider, the operating frequency of said first oscillator being twice the first pulse frequency, and wherein the second means includes a second oscillator in series with a second frequency divider, the operating frequency of said second oscillator being twice the second pulse frequency.

9. The apparatus of claim 5 including means for simultaneously varying the intensity of pulses produced by the first and second means.

10. The apparatus of claim 5 wherein the first and second means produce first and second pulse frequencies which are non-mixing frequencies.

11. The apparatus of claim 10 wherein the first pulse frequency is approximately 2300 cycles per second and the second pulse frequency is approximately 3900 cycles per second.

12. The apparatus of claim 5 wherein the first means produces pulses of electromagnetic radiation having a wavelength in the red range and wherein the second means produces pulses of electromagnetic radiation having a wavelength in the infrared range.

13. Testing apparatus comprising:
(a) exposing means for exposing a test specimen to electromagnetic radiation of two different wavelengths, said means including:
 (i) first means for generating pulses of electromagnetic radiation having the first of the two different wavelengths, said pulses being generated at a first pulse frequency;
 (ii) second means for generating pulses of electromagnetic radiation having the second of the two different wavelengths, said pulses being generated at a second pulse frequency; and
 (iii) means for simultaneously exposing the test specimen to the first and second pulses; and
(b) means for detecting the intensity of electromagnetic radiation at each of the two different wavelengths at a selected location in the vicinity of the test specimen, said means including:
 (i) transducer means at the selected location for producing an electrical signal which is representative of the intensity of electromagnetic radiation in the vicinity of said means, said transducer means being responsive to electromagnetic radiation of the first and second wavelengths: and
 (ii) means for separating the electrical signal produced by the transducer means into first and second electrical signals which are representative of the intensity of electromagnetic radiation in the vicinity of the transducer means at the first and second wavelengths, respectively, said means including first bandpass filter means centered at or near the first pulse frequency for producing the first electrical signal and second bandpass filter means centered at or near the second pulse frequency for producing the second electrical signal.

14. The apparatus of claim 13 wherein said means for separating includes means for demodulating the electrical signals produced by the first and second bandpass filters.

15. The apparatus of claim 14 wherein said means for demodulating includes a half-wave rectifier in series with a low pass filter.

16. The apparatus of claim 13 wherein the first means includes a first oscillator in series with a first frequency divider, the operating frequency of said first oscillator being twice the first pulse frequency, and wherein the second means includes a second oscillator in series with a second frequency divider, the operating frequency of said second oscillator being twice the second pulse frequency.

17. The apparatus of claim 13 wherein the first and second means produce first and second pulse frequencies which are non-mixing frequencies.

* * * * *